US009086396B2

(12) United States Patent
Burkard

(10) Patent No.: US 9,086,396 B2
(45) Date of Patent: Jul. 21, 2015

(54) SYSTEM AND METHOD FOR THE AUTOMATED PROCESSING OF FLUIDS, METHOD FOR DETERMINING THE MATCHING OF OBJECTS

(75) Inventor: Daniel Burkard, Huenenberg See (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 1005 days.

(21) Appl. No.: 12/623,797

(22) Filed: Nov. 23, 2009

(65) Prior Publication Data

US 2010/0132438 A1 Jun. 3, 2010

(30) Foreign Application Priority Data

Nov. 28, 2008 (EP) .................................... 08170313

(51) Int. Cl.
| | |
|---|---|
| *G01N 35/00* | (2006.01) |
| *G01N 35/10* | (2006.01) |
| *G01N 1/10* | (2006.01) |
| *B06B 1/00* | (2006.01) |

(52) U.S. Cl.
CPC ................................ *G01N 35/1011* (2013.01)

(58) Field of Classification Search
CPC ............. G01N 2035/0493; G01N 2035/0494; G01N 35/10; G01N 2035/1011; G01N 2035/1058; G01N 2203/0658; B01J 19/006; B01J 19/10
USPC .......... 422/67, 68.1, 510, 105–108, 110, 112, 422/127–128; 436/43, 49–50, 55, 148–149, 436/174, 180; 73/863.32, 864, 864.01
See application file for complete search history.

(56) References Cited

U.S. PATENT DOCUMENTS

| | | | | | |
|---|---|---|---|---|---|
| 5,465,629 | A | * | 11/1995 | Waylett, Jr. ................. | 73/864.24 |
| 6,060,022 | A | * | 5/2000 | Pang et al. ...................... | 422/65 |
| 6,200,287 | B1 | * | 3/2001 | Keller et al. ................. | 604/6.01 |
| 6,535,824 | B1 | * | 3/2003 | Mansky et al. .................... | 506/8 |
| 6,764,860 | B2 | * | 7/2004 | Lee ............................... | 436/518 |
| 6,878,346 | B2 | | 4/2005 | DeYoung et al. | |
| 6,962,675 | B2 | * | 11/2005 | Lewis et al. ..................... | 422/83 |
| 7,354,415 | B2 | * | 4/2008 | Bainbridge et al. ......... | 604/6.01 |
| 7,611,908 | B2 | * | 11/2009 | Miller et al. .................. | 436/526 |
| 7,618,589 | B2 | * | 11/2009 | Toi et al. ....................... | 422/561 |

(Continued)

FOREIGN PATENT DOCUMENTS

| | | |
|---|---|---|
| EP | 0 732 598 A1 | 3/1996 |
| EP | 0 979 998 A2 | 7/1999 |

(Continued)

*Primary Examiner* — Brian R Gordon
(74) *Attorney, Agent, or Firm* — Faegre Baker Daniels LLP

(57) ABSTRACT

A system and method for the automated processing of fluids according to a process operation plan involving the use of preloaded objects, which are to be present in target object positions, are disclosed. The system includes: a processing area in which objects to be used for the processing of fluids are located; at least one ultrasonic sensor for determining the presence of objects by acoustical waves; a positioning device to which the ultrasonic sensor is fixed and which moves the ultrasonic sensor in at least one direction relative to the processing area; a control computer determining the presence of objects and determining if objects are present in target object positions in the processing area as defined by the process operation plan; a pipetting device for pipetting of fluids between cavities located in the processing area; and an analytical or pre-analytical processing device for processing of fluids located in the processing area.

7 Claims, 7 Drawing Sheets

(56) References Cited

U.S. PATENT DOCUMENTS

| | | | |
|---|---|---|---|
| 7,648,844 B2 * | 1/2010 | Srivastava et al. | 436/526 |
| 7,666,355 B2 * | 2/2010 | Alavie et al. | 422/65 |
| 7,985,375 B2 * | 7/2011 | Edens et al. | 422/64 |
| 8,007,723 B2 * | 8/2011 | Ikushima | 422/67 |
| 8,088,329 B2 * | 1/2012 | Hutchins et al. | 422/63 |
| 8,353,619 B2 * | 1/2013 | Laugharn et al. | 366/127 |
| 8,357,538 B2 * | 1/2013 | Self et al. | 422/63 |
| 8,394,321 B2 * | 3/2013 | Franzoni et al. | 422/44 |
| 2002/0192117 A1 * | 12/2002 | Lewis et al. | 422/82.05 |
| 2006/0210435 A1 * | 9/2006 | Alavie et al. | 422/65 |
| 2007/0224700 A1 * | 9/2007 | Masters | 436/501 |
| 2008/0050289 A1 | 2/2008 | Laugharn, Jr. et al. | |
| 2008/0056942 A1 * | 3/2008 | Arima et al. | 422/63 |
| 2008/0247914 A1 * | 10/2008 | Edens et al. | 422/100 |
| 2009/0000351 A1 * | 1/2009 | Magnussen et al. | 73/1.74 |
| 2009/0246085 A1 * | 10/2009 | Watson et al. | 422/100 |
| 2010/0126286 A1 * | 5/2010 | Self et al. | 73/863.81 |
| 2010/0229659 A1 * | 9/2010 | Ikushima | 73/864.11 |
| 2010/0233031 A1 * | 9/2010 | Masters | 422/69 |
| 2010/0233824 A1 * | 9/2010 | Verhoeckx et al. | 436/501 |
| 2010/0297780 A1 * | 11/2010 | De Theije et al. | 436/526 |
| 2010/0330698 A1 * | 12/2010 | Evers | 436/501 |
| 2011/0014719 A1 * | 1/2011 | Sijbers et al. | 436/150 |
| 2011/0318845 A1 * | 12/2011 | Kurono et al. | 436/174 |
| 2012/0156765 A1 * | 6/2012 | Wimberger-Friedl et al. | 435/287.1 |
| 2013/0040850 A1 * | 2/2013 | Sigal | 506/9 |
| 2013/0109030 A1 * | 5/2013 | Hardeman et al. | 435/7.1 |
| 2013/0177922 A1 * | 7/2013 | Laugharn et al. | 435/7.1 |

FOREIGN PATENT DOCUMENTS

| | | |
|---|---|---|
| EP | 0 979 999 A2 | 7/1999 |
| EP | 1 975 626 A1 | 10/2008 |
| EP | 1975629 A1 | 10/2008 |
| JP | 2004317211 A | 11/2004 |
| WO | 2007 039524 A2 | 4/2007 |

* cited by examiner

SYSTEM AND METHOD FOR THE AUTOMATED PROCESSING OF FLUIDS, METHOD FOR DETERMINING THE MATCHING OF OBJECTS

TECHNICAL FIELD

Embodiments of the present invention relate generally to automated systems for the analytical or pre-analytical processing of fluids, and more particularly to a system and method for the automated processing of fluids according to a process operation plan involving the use of preloaded objects. It further relates to a method for determining the matching of objects in an instrument with preloaded objects to be present in target object positions according to a process operation plan.

BACKGROUND

In these days, various types of clinical analyzers for the automated processing of biological fluids such as blood, serum and urine are being in practical use. Sample preparation and analysis of biological fluids basically involves handling and mixing of the fluids using various components such as multi-well plates, pipette trays, pipette tips and bottles filled with reagents, buffers, wash solutions and the like, which may be subsumed by the generic term "consumables". When operable in a standalone mode, analyzers typically are manually preloaded with consumables needed for the processing of fluids prior to starting the automated fluid processing.

Since there is a strong demand for offering a wide variety of analytical options and with a view to improve effectiveness in sample processing, analyzers often process samples in parallel and/or split each sample into a number of sample aliquots for the simultaneous processing thereof deploying different analytical techniques. Due to the high sample throughput and dependent on the number of analytical options offered, modern apparatus are subject to an elevated consumption of consumables which they have to be charged with.

However, in daily routine, a problem may occur that consumables needed for the automated processing of fluids are misplaced or even missing because of human error when manually preloading the analyzer. Albeit, even in case of automatically preloading of consumables, since there is a risk of dropping or misplacing of objects due to misalignment errors, misplacement or absence of consumables cannot be excluded. This especially applies to the case of modern analyzers which, according to the above, normally are subject to an elevated consumption of consumables requiring many preloading operations.

In modern analyzers, missing or misplaced consumables will automatically cause a stop of a current run which entails a delay for starting the next run and may also give rise to repeat the aborted run which lowers efficiency in fluid processing. Even worse, accidental stops may constitute a need to discard the fluid samples currently processed, which has to be avoided since some fluids require delicate extraction operations or are unique in a sense that they cannot be reproduced such as in forensic applications.

SUMMARY

It is against the above background that embodiments of the present invention provide a system and method for the automated processing of fluids involving the use of preloaded consumables to enable reliable fluid sample processing without a risk of interrupting an ongoing run due to missing or misplaced consumables.

In one preferred embodiment, a system for the automated processing of fluids according to a process operation plan involving the use of preloaded objects, said process operation plan defining preloaded objects to be present in target object positions, is disclosed. The system comprises: a processing area in which objects to be used for the processing of fluids are located; at least one ultrasonic sensor for determining the presence of objects by acoustical waves; a positioning device to which the ultrasonic sensor is fixed and which moves the ultrasonic sensor in at least one direction relative to said processing area; a control computer determining the presence of objects and determining if objects are present in target object positions in said processing area as defined by said process operation plan; at least one pipetting device for pipetting of fluids between cavities located in said processing area; and an analytical or pre-analytical processing device for processing of fluids located in said processing area.

In another preferred embodiment, a method is disclosed for determining the matching of objects present in a processing area in an instrument with preloaded objects to be present in target object positions in said instrument according to a process operation plan. The method comprises: determining the presence of objects relative to the processing area in said instrument by means of at least one ultrasonic sensor; and determining if objects are present in target object positions as defined by said process operation plan.

Other and further embodiments, features and advantages of the invention will appear more fully from the accompanying drawings, the following detailed description, and the appended claims.

BRIEF DESCRIPTION OF THE DRAWINGS

In the drawings, like designations denote like or similar elements, and in which.

REFERENCE LIST

Figure 1:
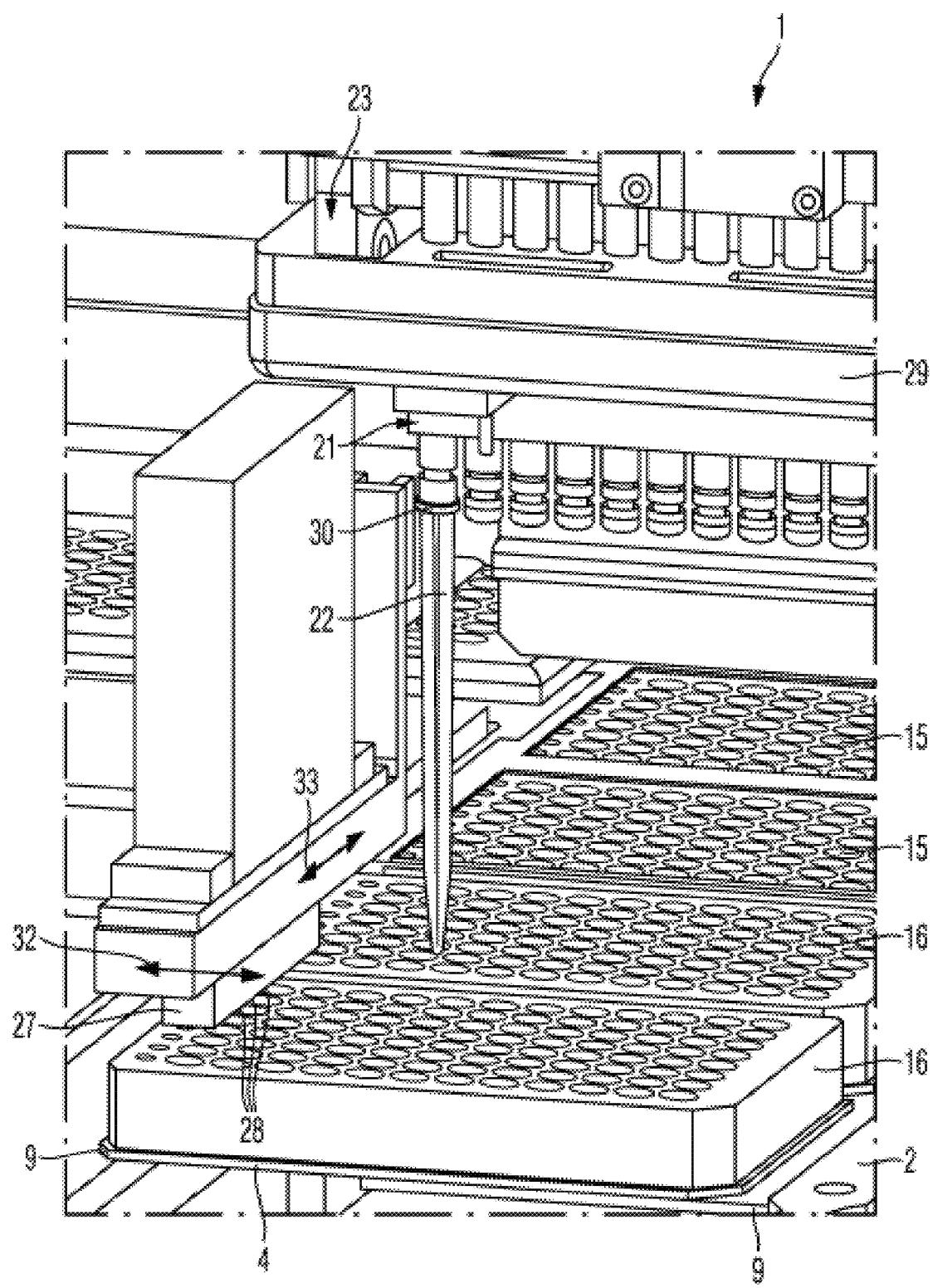
FIG. 1 is an elevational partial view illustrating an exemplary embodiment of the system of the invention, adapted for the extraction of nucleic acids.

1 System
2 Work-plate
3 Waste rack
4 Processing rack
5 Tip tray rack
6 First reagent rack
7 Second reagent rack
8 Bottle rack
9 Rib
10 Rack opening
11 Front side 12 Retaining section
13 Waste tip tray
14 Waste liquid tray
15 Processing plate
16 Output plate
17 Tip tray
18 Reagent plate
19 Bottle cartridge
20 Bottle
21 First pipettor
22 Pipetting tip
23 Positioning device
24 First guiding rail
25 Second guiding rail
26 Second pipettor
27 Sensor array
28 Ultrasonic sensor
29 Transfer head
30 First pipette
31 Second pipette
32 Arrow
33 Arrow
34 Control computer
35 Display
36 Processing device
37 Reagent

DETAILED DESCRIPTION

According to one embodiment of the invention, a system for the automated analytical or pre-analytical processing of fluids (fluid samples) according to a process operation plan involving the use of preloaded objects for automatically processing the fluids is provided. The process operation plan which may be embodied as a computer program for running on a programmable control computer instructs operations to be performed for automatically processing the fluids. Specifically, the process operation plan defines objects which are required for the automated processing of fluids and, thus, have to be preloaded in advance of starting the automated processing of fluids. The process operation plan also defines target object positions for each of the objects to be preloaded in advance of starting the automated processing of fluids, that is to say, it defines object positions into which the objects are intended to be preloaded prior to starting the automated processing of fluids.

Accordingly, a system for the automated processing of fluids is provided, which comprises a processing area in which objects to be used for the processing of fluids are located. As used herein, the term "processing area" describes an area of the system, in which the automated processing of fluids is being performed.

The system further comprises at least one ultrasonic sensor, adapted for determining the presence of objects in said processing area by means of acoustic waves. Ultrasonic sensors for emitting ultrasonic waves towards an object of measurement and receiving acoustic waves returning upon reflection at the object are well-known to those of skill in the art, and, for instance, are described in European patent specification EP 0732598 B1. Accordingly, an ultrasonic sensor includes at least one transducer used for emitting of acoustic waves in a transmitting mode and receiving of reflected acoustic waves in a receiving mode, which modes may be changed by a change-over switch. More specifically, in transmitting mode, drive pulses may be fed to the transducer to generate acoustic waves emitted to the object of measurement. On the other hand, in receiving mode, the transducer detects reflected acoustic waves which, for instance, are fed to a sampling circuit to be sampled at a predetermined frequency and to then be converted into digital data.

The system further comprises a positioning device to which the at least one ultrasonic sensor is fixed, adapted to move the ultrasonic sensor in at least one direction relative to the processing area. For that purpose, the ultrasonic sensor is fixed to a positioning member (e.g. a transfer head) of the positioning device.

The system further comprises a control computer for controlling of the automated processing of fluids according to the process operation plan which, for instance, may be embodied as a programmable control computer running a computer-readable program provided with instructions to perform operations in accord with the process operation plan. The control computer may, e.g., include functional entities such as microprocessors dedicated to the control of specific system components under main control of the control computer. The functional entities may be integrated in these system components. In that, the control computer is electrically connected to the system components which require control as specified by the process operation plan which include the positioning device and the ultrasonic sensor. The control computer receives information from the different components of the system and generates and transmits corresponding control signals for controlling the components according to the process operation plan. The control computer can be connected to the system components via one or more data connections, e.g., by use of a wired or wireless network.

More particularly, in the system of the invention, the control computer is being configured to determine the presence of objects and to determine if objects are present in target object positions in said processing area as defined by said process operation plan. In that, the control computer may generate control signals for coordinating movements of the at least one ultrasonic sensor relative to the processing area and, by means of the ultrasonic sensor, determining if objects to be used for the automated processing of fluids are present in the target object positions as defined by the process operation plan.

The control computer may, for instance, be configured in a way that determination of the presence of individual objects is based on determining a difference of signal values (e.g. time between emission of acoustic waves and reception of reflected acoustic waves) between first and second signals values, with first signal values corresponding to acoustic waves reflected from surfaces located at least in the target object positions and with second values corresponding to acoustic waves reflected from surfaces located in reference positions. The reference positions preferably are provided by surfaces of the holder.

Alternatively, the control computer may, for instance, be configured in a way that determination of the presence of individual objects is based on determining of differences of distances between first and second distances of surfaces reflecting the first and second acoustic waves, respectively.

The control computer may be configured to determine the presence of objects and determining if objects are present in target object positions as defined by said process operation plan performing a control run in advance of starting the automated processing of fluids and/or during the automated processing of fluids.

The control computer may be configured to generate control signals to determine an identity and/or an orientation of individual objects as determined by the process operation plan, for instance, in determining an object profile (pattern), in particular a height profile, of the object concerned and comparing the object profile as determined with an object profile as defined by the process operation plan.

The control computer may also be configured to generate control signals based on a result of the determination if objects are present in target object positions as defined by the process operation plan which are supplied to a signalizing device, e.g. a display, to generate a user-identifiable message, so that a user may be informed about lacking and/or misplaced objects for use in the automated fluid processing. The message may, for instance, contain information for guiding a user for manually or automatically loading of missing and/or misplaced objects to be used in fluid processing as defined by the process operation plan.

Specifically, the control computer may, e.g., be configured to control the signalizing device in a manner to signalize a mismatch (difference) between objects actually present and objects required at target object positions as defined by the process operation plan.

Specifically, the control computer may, e.g., be configured to control a display in a manner to display a (e.g. schematic) representation of one or more parts of the system in order to visualize the target object positions as defined by the process operation plan. In that, the display can, e.g., be controlled to display one or more parts of the processing area. More specifically, the control computer may, e.g., be configured to control the display in a manner to display a mismatch (difference) between objects actually present and objects required at target object positions as defined by the process operation plan.

Otherwise, the control computer may be configured to control the display in a manner to display the objects at target object positions as defined by the process operation plan, followed by displaying a mismatch between objects actually present and the objects required at target object positions as defined by the process operation plan, e.g. after detecting a manipulation of the system and/or after elapse of a pre-determined time span, in order to display the result of a manual and/or automatic loading operation for charging the system with the required objects.

Specifically, the process operation plan may include a section which guides a user in loading the system with objects. Such a section for user guidance may involve the display of a representation of the processing area of the system and the objects to be loaded on a display. The process operation plan may further comprise a section for signalling loading mistakes to the user to facilitate ramification of the loading mistakes.

The system further comprises at least one pipetting device for pipetting of fluids between cavities located in the processing area.

The system yet further comprises at least one analytical or pre-analytical processing device for processing of fluids located in the processing area. Analytical processing devices which are being used for analytically processing the fluids typically include a light source illuminating sample fluids and a detector receiving radiation emitted, transmitted or reflected from the sample such as colorimetric measuring units, fluorescence measuring units and the like. Further, electrical measuring devices such as coulometric, conductometric or potentiometric (e.g. ion-selective electrodes) measuring devices can be employed. Pre-analytical processing devices which are being used for pre-analytically processing the fluids (prior to analytically processing the fluids) typically include heating or incubation devices, magnetic separation devices, centrifugation devices, dilution and aliquotation units. As above-detailed, functional entities of the control computer can, e.g., be integrated in the analytical or pre-analytical processing device for the control thereof. Otherwise, the control computer is being connected to the analytical or pre-analytical processing device, e.g., by means of a network.

The system may further comprise at least one holder, adapted to hold the objects to be used for the automated processing of fluids in the target object positions as defined by the process operation plan. The holder may, for instance, be embodied as a movable rack which can be moved into an inoperative position for loading/unloading with objects and an operative position for use of the preloaded objects when performing the automated processing of fluids. In that, the holder preferably holds a multi-well plate provided with cavities having defined positions. The holder is preferably kept stationary during determining of the presence of objects.

Hence, enabling an automated determination if objects are present in target object positions as defined by the process operation plan advantageously allows for highly reliable automated processing of fluids which especially applies to the case of modern instruments requiring frequent preloading operations which are likely to cause errors as per missing or misplaced objects.

The system for the automated processing of fluids may be configured in various ways in accordance with the specific demands of users as long as automated processing of fluids involves the use of preloaded objects. In that, the system for automatically processing of fluids may be embodied as analyzer for analyzing of fluids typically involving mixing of the fluids with reagents to determine presence and amount or absence of specific substances contained in the fluids. It may also be embodied as a pre-analytic sample preparator for the automated preparation of fluid samples prior to analysis such as an extractor for the automated extraction of nucleic acids prior to amplification.

Fluids to be automatically processed in the system may include biological fluids (e.g. blood, serum, urine, cerebrospinal fluids and nucleic acids (DNA/RNA) containing fluids), non-biological fluids (e.g. chemical compounds and drugs) and any other fluid of interest as long as automated processing thereof involves the use of preloaded objects.

The term "processing of fluids" as used herein may relate to a single-step process for automatically processing of fluids so that objects to be used for the automated processing of fluids are being preloaded in advance of starting the automated processing of fluids. It may also relate to a multi-step process for automatically processing of fluids in which objects to be used for the automated processing of fluids are being preloaded in advance of starting the first step and/or during a time-interval in-between consecutive process steps. In the latter case, starting of the automated processing of fluids may either relate to starting the multi-step process or starting of any individual process step thereof.

The term "preloading" of objects as used herein refers to any manual and/or automated loading operation in advance of starting the automated processing of fluids to be kept in readiness for use in the automated processing of fluids. Automated loading of objects may be performed using a manipulator such as a robotic arm. Automatically loading of objects requires control, since problems as to missing or misplaced objects may occur, for instance, in case objects remain sticking on the robotic arm.

Objects to be used for the automated processing of fluids most typically are disposables which include plates forming cavities such as multi-well plates, pipette trays for receiving pipette tips, pipette tips and containers containing various liquids such as reagents, suspensions of magnetically attractable particles, buffers, wash solutions and the like.

It may be preferred that the system comprises a plurality of ultrasonic sensors which are arranged in a linear (one-dimensional) or planar (two-dimensional) array for simultaneously determining the presence of objects. In that case, the control computer is configured to coordinate a plurality of ultrasonic sensors in parallel to simultaneously determine the presence of objects, advantageously increasing efficiency in sample processing which results in an increased sample throughput and reliability.

In the above embodiment, it may be preferred to arrange a plurality of ultrasonic sensors in a linear array extending in a first direction in accord with a planar array of objects extending in the first direction and a second direction with are in orthogonal relationship with respect to each other, wherein the inter-distance of ultrasonic sensors corresponds to the inter-distance of objects in the first direction. Particularly, a number of ultrasonic sensors may correspond to an integer divisor of a number of objects. In that case, a planar array of objects may be efficiently controlled to determine if objects are present in target object positions as defined by the process operation plan. Specifically, the control computer may be configured to control determining of the presence of objects based on determining a difference of signal values between first and second signals values, with the first signal values corresponding to acoustic waves reflected from surfaces at least located in the target object positions and a second signal value corresponding to acoustic waves reflected from a surface as given by the plane the objects are arrayed in. Using such reference plane, errors in determining presence of objects due to varying positioning of the ultrasonic sensor relative to the holder may advantageously be avoided.

According to another preferred embodiment of the system of the invention, the system further comprises a pipetting device which is provided with at least one pipette for pipetting of liquids for the automated processing of fluids. In that case, the positioning device preferably is adapted for moving both the at least one ultrasonic sensor and the at least one pipette for pipetting of liquids. Preferably the at least one ultrasonic sensor and the at least one pipette are both fixed to the same positioning device. The use of a single positioning device saves costs and space, avoids a risk of collision between different positioning devices and simplifies control thereof. On the other hand, configuring the control computer in a way that moving of the at least one ultrasonic sensor for determining the presence of objects is combined with moving of the at least one pipette for pipetting of liquids for the automated processing of fluids, efficiency in the automated processing of fluids may be increased.

According to another embodiment of the invention, a method is provided for determining the matching of objects present in a processing area in an instrument with preloaded objects to be present in target object positions in the instrument according to a process operation plan. The method may comprise the following steps.

A step of determining the presence of objects relative to the processing area in the instrument by means of at least one ultrasonic sensor. Such step may include moving the at least one ultrasonic sensor relative to the processing area in the instrument.

A step of determining if objects are present in target object positions as defined by the process operation plan.

The above method of the present invention advantageously allows for an automated control of presence of objects in the intended target object positions in the processing area as defined by the process operation plan.

In case of mismatch between the presence of objects as defined by the process operation plan and the actual presence of objects, preferably a step of outputting a message based on the result of the determination to a signalizing device such as a display is performed. The message may, e.g., contain user-guiding information for guiding a user with respect to loading of missing and/or misplaced objects to be loaded into the instrument.

Specifically, the signalizing device can, e.g., be controlled to signalize a mismatch between the objects present and objects required in target object positions as defined by the process operation plan. More specifically, a display can, e.g., be controlled to display a representation of one or more parts of the system, which e.g. can be one or more parts of the processing area, in order to visualize the target object positions as defined by the process operation plan. In that, the display can, e.g., be controlled to display the objects required at target object positions as defined by the process operation plan. Otherwise, the display can also be controlled to display a mismatch between objects actually present and objects required in target object positions as defined by the process operation plan. The display can, e.g., be controlled to display the objects required at the target object positions as defined by the process operation plan, followed by displaying a mismatch between objects actually present and objects required in target object positions as defined by the process operation plan, e.g. after detecting a manipulation of the system and/or after elapse of a pre-determined time span, in order to display the result of a manual and/or automatic loading operation for charging the system with the required objects.

According to a preferred embodiment of the method of the invention, determining of presence of objects involves measuring of first signal values (e.g. time between emission of acoustic waves and reception of reflected acoustic waves) of first acoustic waves received upon reflection at surfaces at least in the target object positions and comparing the first signal values with at least one second signal value received upon reflection at a surface in a reference position.

According to another preferred embodiment of the method of the invention, determining of presence of objects involves measuring of first distance values of acoustic waves received upon reflection at surfaces at least in said target object positions and comparing said first distance values with at least one second distance value received upon reflection at a surface in a reference distance position.

According to yet another preferred embodiment of the method of the invention, a step of determining object identities of individual objects and determining if there is matching between object identities as determined and object identities as defined by the process operation plan is performed.

According to yet another preferred embodiment of the method of the invention, a step of determining object orientations of individual objects and determining if there is matching between object orientations as determined and object orientations as defined by the process operation plan is performed.

According to yet another preferred embodiment of the method of the invention, a step of moving a (linear or planar) array of ultrasonic sensors relative to the processing area in the instrument may be performed. Hence, presence of objects may be determined in parallel to thereby advantageously increase efficiency in fluid processing. In particular, in case of a planar array of cavities containing the fluids to be processed, in which the cavities being arranged side by side in a row extending in a first direction and plural rows are stacked one upon the other in a second direction, with the first and second directions being in orthogonal relationship with respect to each other, it may be preferable that a linear array of ultrasonic sensors having the sensors arrayed along the first direction is moved along the first and/or the second direction.

According to yet another preferred embodiment of the method of the invention, moving of the at least one ultrasonic sensor for determining of presence of objects in the processing area is combined with moving of at least one pipette for pipetting of liquids for the automated processing of fluids. Combining movements of the at least one ultrasonic sensor and the at least one pipette, efficiency in sample processing may advantageously be increased.

According to yet another preferred embodiment of the method of the invention, it further includes a step of determining liquid levels of liquids contained in cavities by means of the at least one ultrasonic sensor. Such embodiment advantageously allows for control of liquid levels in order to control presence of fluids and/or outcome of pipetting operations performed in the automated fluid processing. In that case, it may be preferable to determine fluid levels involving measuring of distance values with respect to a reference distance level as defined by a plane of a planar array of cavities.

According to another embodiment of the invention, a method is provided for the automated processing of fluids according to a process operation plan involving the use of preloaded objects which includes a method for determining the matching of objects present in a processing area in an instrument with preloaded objects to be present in target object positions in the instrument according to the process operation plan as above-described.

The embodiments of the present invention will now be described in greater detail below with reference to the accompanying drawings, where like designations denote like or similar elements.

Referring to FIGS. 1 through 7, an exemplary embodiment of the system and method according to the invention is explained. Accordingly, a system 1 (instrument) for the automated processing of nucleic acids containing fluids is described which permits extraction of nucleic acids prior to their amplification. Alternatively, the present invention can be employed in other systems such as in clinical analyzers and the like.

The system 1 includes a horizontal work-plate 2 which may be identified as processing area is provided with a plurality of rack openings 10 arranged side by side with respect to each other, each of which being adapted for accommodating elongated racks 3-8. Each rack opening 10 may be accessed by a slot-like aperture at a front side 11 of the system 1 allowing the racks 3-8 to be inserted into the rack openings 10 and removed therefrom, respectively. For that purpose, each rack 3-8 is provided with two lateral ribs 9 linearly extending in parallel relationship with each other which, when inserting the racks 3-8 into the rack openings 10, get into fitting engagement with grooves formed by the work-plate 2 to slidably support the racks 3-8.

Figure 2:
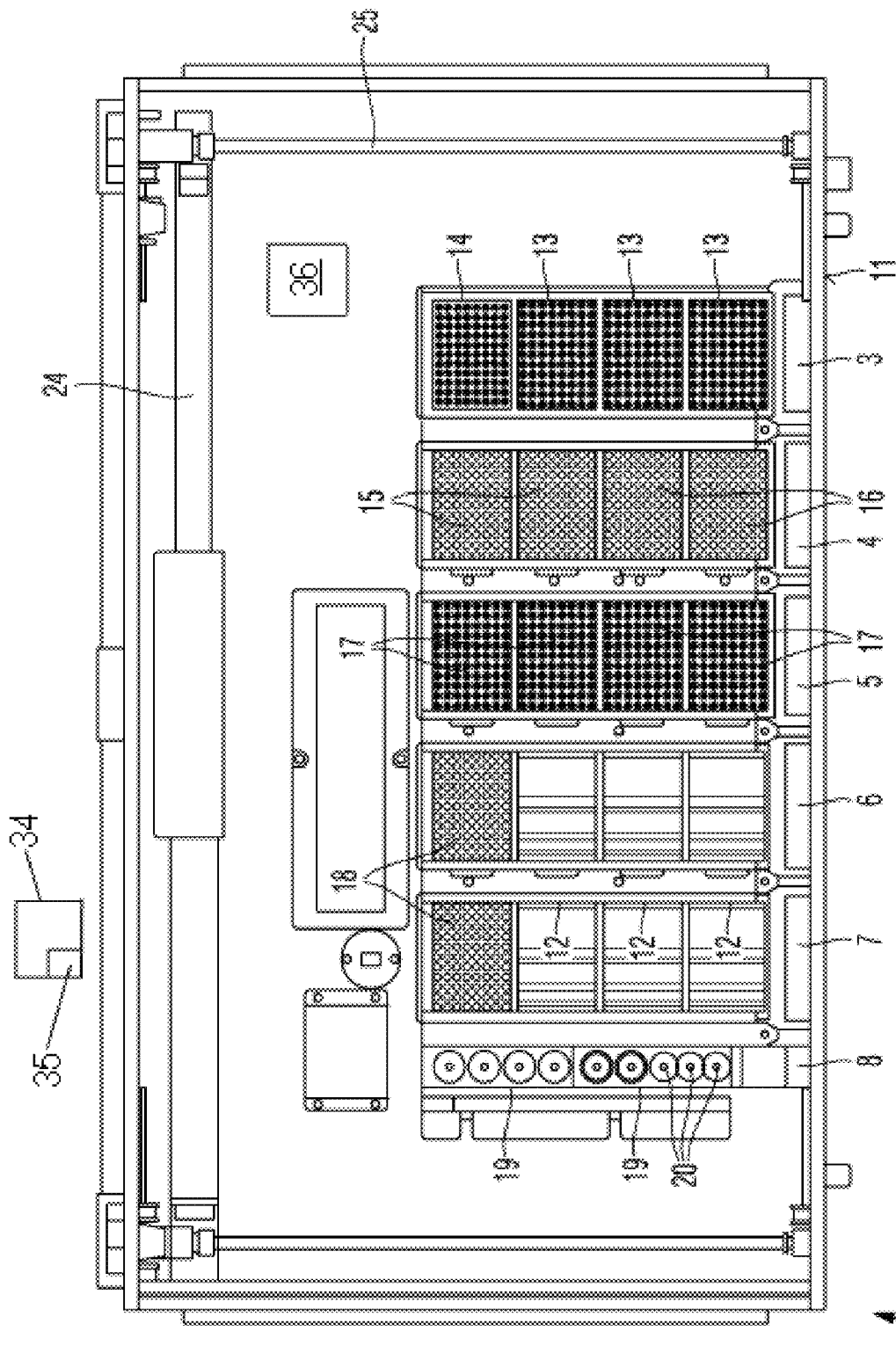
FIG. 2 is a top view of the system of FIG. 1.

The system 1 comprises a number of six racks 3-8 including a waste rack 3, a processing rack 4, a tip tray rack 5, a first reagent rack 6, a second reagent rack 7 and a bottle rack 8. Individual racks are being provided with a number of retaining sections 12 to accommodate and hold various objects such as multi-well plates, tip trays and bottle cartridges, and thus define various target object positions with the system 1. In FIG. 2, the waste rack 3 is shown to be loaded with three waste tip trays 13 to receive waste tips and a waste liquid tray 14 to receive waste liquid, the processing rack 4 is shown to be loaded with two processing plates 15 (deep-well plates) to receive nucleic acids containing fluids used as starting materials for the extraction of nucleic acids and two output plates 16 to receive solutions containing the extracted (purified) nucleic acids, the tip tray rack 5 is provided with four tip trays 17 filled with tips, the first and second reagent racks 6, 7 may be loaded with various processing solutions such as buffer and wash solutions (not further detailed in the figures) and are shown to be loaded with reagent plates 18 for mixing of reagent containing solutions, and the bottle rack 8 is provided with several bottle cartridges 19 for supporting of bottles 20 containing various liquids such as enzymes and suspensions of magnetic particles.

Accordingly, the racks 3-8 are provided with plural consumables to be used for the automated extraction of nucleic acids which have to be manually or automatically preloaded prior to starting the extraction of nucleic acids. For that purpose, individual racks 3-8 can be partly or completely put out of the rack openings 10 for manual or automated loading and/or unloading operations as above-detailed. For the purpose of illustration only, in FIG. 3, the processing rack 4 is shown to be partly pulled out of the rack opening 10.

Figure 3:
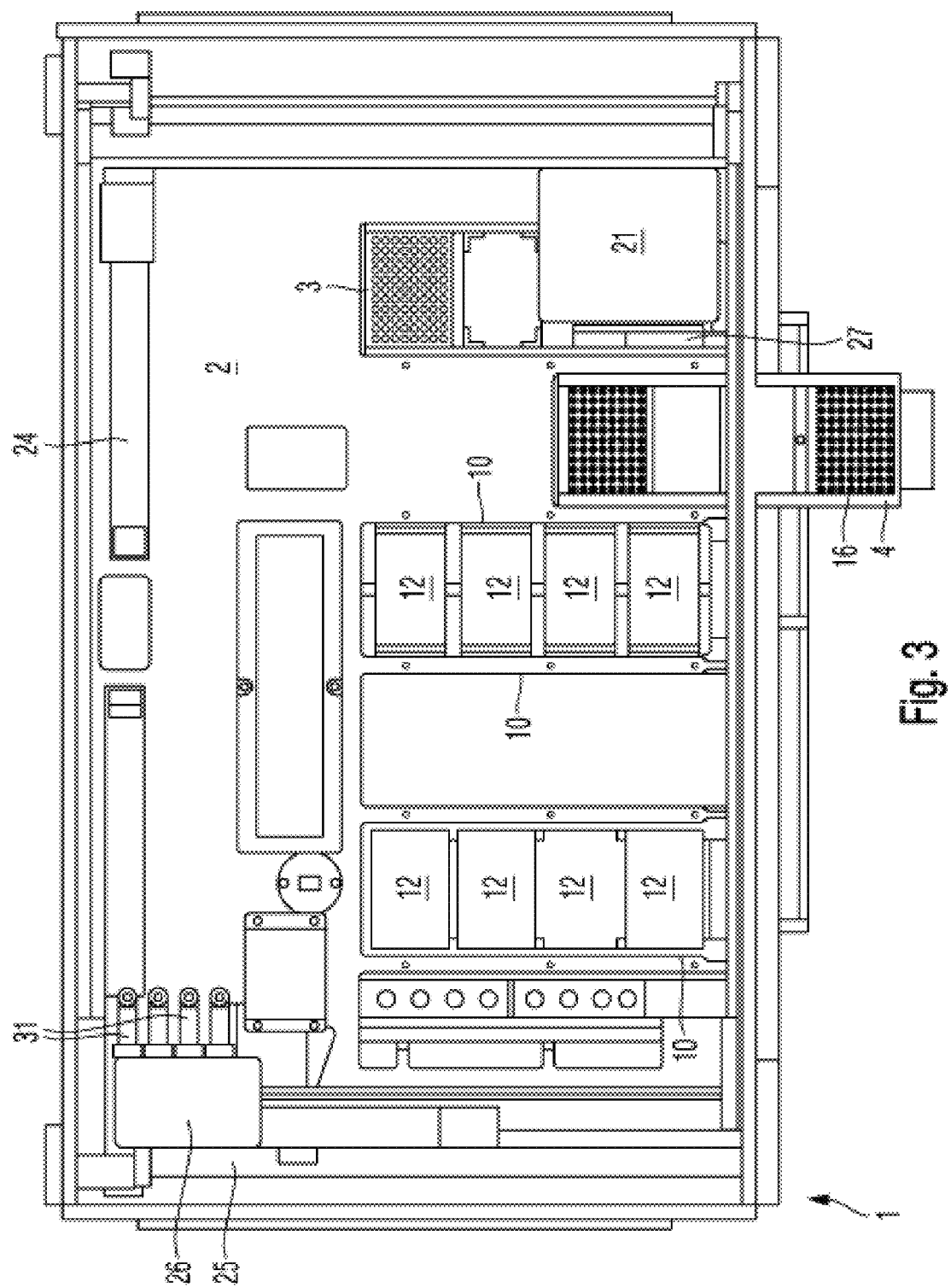
FIG. 3 is another top view of the system of FIG. 1.

While FIGS. 2 and 3 depict specific numbers of system components such as racks, retaining sections, plates, trays and bottle cartridges, it is to be understood that these numbers may vary in accord with specific needs for the extraction of nucleic acids.

As exemplified in the present embodiment, individual plates are provided with a planar array of 96 wells with 8 wells arranged side by side in a row extending in a first direction and 12 rows stacked one upon the other in a second direction, with the first and second directions being in orthogonal relationship with respect to each other. Consistently therewith, individual tip trays include 96 tips. It, however, is to be understood that differently sized arrays may alternatively be used in accordance with specific needs for the extraction of nucleic acids.

The system 1 comprises a first pipettor 21 including 96 first pipettes 30 provided with disposable pipetting tips 22, adapted to transfer fluids to or from the plates. More specifically, the first pipettes 30 are mounted to a transfer head 29 of a positioning device 23 which can be moved in a first direction of travel towards and away from the work-plate 2, for instance by means of a spindle drive, and in second and third directions of travel in a plane, with the second and third directions being in orthogonal relationship with respect to the first direction, by means of first and second guiding rails 24, 25. Since such positioning device 23 is well-known to those of skill in the art, it is not further detailed herein. The first pipettor 21 can thus be moved relative to the racks 3-8 for pipetting of liquids for the automated processing of fluid samples.

The system 1 further includes a second pipettor 26 including a plurality of second pipettes 31, adapted to transfer fluids to or from the plates, which is not further detailed herein.

The system yet further includes a linear array 27 of eight ultrasonic sensors 28, adapted to determine the presence of objects by means of acoustic waves which are secured to the transfer head 29 and thus can be moved together with the first pipettor 21 with respect to the racks 3-8. Stated more particularly, the linearly arrayed ultrasonic sensors 28 extend along the same direction (first direction) as each row of individual plates, wherein a distance in-between adjacent ultrasonic sensors 28 matches a distance in-between adjacent wells.

A programmable control computer 34 is used for controlling of the automated processing of nucleic acids containing fluids for the extraction of nucleic acids according to a predetermined process operation plan. Accordingly, the control computer 34 runs a computer-readable program which is provided with instructions to perform automated operations in accord with the process operation plan. In that, the control computer 34 is electrically connected to the system components which require control as specified by the process operation plan which include the positioning device 23 and the ultrasonic sensors 28. Data connection between the control computer 34 and the system components is by plural data connections (not illustrated) which can be part of a network for transferring data. The control computer 34 may be an off-the-shelf computer programmed to run the process operation plan for controlling the system 1.

Aside from instructing operation steps, the process operation plan defines the consumables which are required for the automated extraction of nucleic acids and thus have to be preloaded in advance of starting the fluid handling steps. In particular, it defines intended positions (target object positions) of consumables with respect to the racks 3-8 into which the consumables are to be placed when preloaded. It also defines intended positions (target object positions) of consumables with respect to individual plates, trays and cartridges into which consumables such as tips and bottles are to be placed when preloaded. The process operation plan may optionally also define identity and/or orientation with respect to the intended position of individual consumables to be used for the automated extraction of nucleic acids.

The control computer 34 further includes a display 35 (signalizing device) for displaying graphical representations and/or messages to be read by the user. In order to enable manual data input, the control computer 34 can, e.g., include a key panel (not illustrated). Otherwise, the display 35 can, e.g., be embodied as touch-screen to display information and enter data.

The system 1 further includes a pre-analytical processing device generally referred to at 36 for processing of fluids located on the work-area 2. The processing device 36, e.g., includes heating and magnetic separation devices (not illustrated) for the automated extraction of nucleic acids. Since extraction of nucleic acids is well-known to those of skill in the art it is not further herein.

Figure 4:
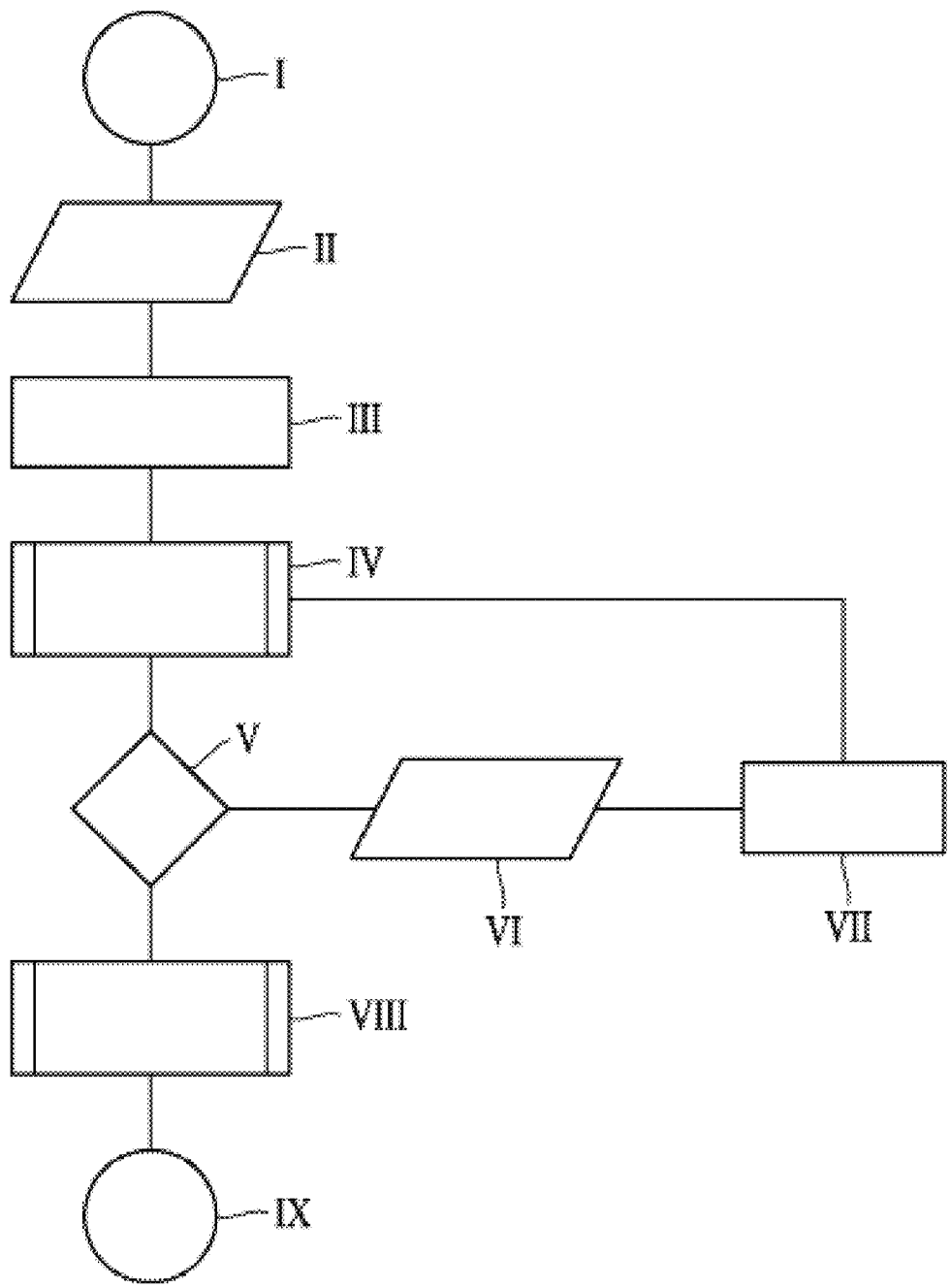
FIG. 4 is a flow chart illustrating exemplary process steps for the processing of nucleic acids containing fluids according to a process operation plan.

Reference is made to FIG. 4 depicting a flow chart illustrating exemplary process steps for the processing of nucleic acids containing fluids according to the process operation plan.

The symbols of the flowchart have the following meaning:
I: START
II: DISPLAY PROCESS OPERATION PLANS
III: SELECT A PROCESS OPERATION PLAN
IV: START SUBROUTINES "CHECK PRESENCE AND FLUID LEVEL"
V: MISMATCH?
VI: DISPLAY MESSAGE
VII: INITIATE RE-START SUBROUTINE "CHECK PRESENCE AND/OR FLUID LEVEL"
VIII: START SUBROUTINE "EXTRACTION"
XI: END Accordingly, beginning with starting the process (process step I), e.g., when powering-up system 1, different process operation plans are displayed (process step II) on the display 35 for selection by a user. After manually and/or automatically preloading various consumables and the nucleic acids containing solutions, actuating the control computer 34, the user can select a process operation plan according to the specific operations to be performed for the processing of nucleic acids containing fluids (process step III).

As above-detailed, the process operation plan defines the consumables which are to be used for the processing of nucleic acids containing fluids, as well as target positions, identities and orientations with respect to the intended position of individual consumables. It may be provided that the user can also enter various process parameters for tailoring the process operation plan to specific needs.

Having a process operation plan selected as desired, a subroutine "CHECK PRESENCE" (process step IV) starts. This subroutine starts a control run in which the sensor array 27 of ultrasonic sensors 28 is moved over the racks 3-8 to determine if consumables are present in their intended positions as defined by the process operation plan.

For the purpose of illustration only, it is now assumed that, according to the process operation plan, the extraction of nucleic acids needs two processing plates 15 filled with nucleic acids containing solutions and four tip trays 17 filled with pipetting tips to be placed in the corresponding retaining sections 12 of the processing rack 4 and tip tray rack 5, respectively, which thus define target object positions.

The display 35 can, e.g., display the work-plate 2 or one or more parts thereof to visualize the consumables at their intended positions required for the processing of the fluids, i.e. extraction of nucleic acids. Hence, based on this visual information, the user can readily charge the system 1 with the required consumables. Charging of the system 1 with consumables can be performed by manual and/or automatic charging operations.

In order to determine the presence of objects, the ultrasonic sensors 28 are moved over the intended locations of the tip trays 17 by means of the transfer head 29. Stated more particularly, when moving the ultrasonic sensors over the tip trays 17, first acoustic waves are generated and emitted towards the intended locations of the processing plates 15, with first signals (time between emission of acoustic waves and reception of reflected acoustic waves) of the reflected first acoustic waves being measured. Furthermore, at least one second acoustic wave is generated and emitted towards a predetermined surface (such as a dedicated reference surface) of the tip tray rack 5, with a second signal (time between emission of acoustic waves and reception of reflected acoustic waves) of the reflected second acoustic wave being measured. The determination of the presence of the tips contained in the tip trays 17 is similarly performed, except for emitting the at least one second acoustic wave towards a predetermined surface of each of the tip trays 17 and measuring second signals of the second acoustic waves reflected therefrom.

Similarly, when moving the ultrasonic sensors 28 over the intended locations of the processing plates 15, first acoustic waves are generated and emitted towards the intended locations of the processing plates 15, with first signals (round-trip-times) of the reflected first acoustic waves being measured. Furthermore, at least one second acoustic wave is generated and emitted towards a predetermined surface of the processing rack 4, with a second signal (round-trip-time) of the reflected second acoustic wave being measured.

The determination of the presence of objects is analogously repeated for each of the consumables to be used for processing of nucleic acids containing fluids, with the presence of objects being either determined with respect to the rack to which it belongs or with respect to the plate, tray or cartridge to which it belongs.

Alternatively, the determination of the presence of objects may be based on determining distances of the reflecting surfaces from the ultrasonic sensor based on the resulting round-trip-time (time-of-travel) measurements.

Then a subroutine "CHECK FLUID LEVELS" (process step IV) starts. This subroutine starts a control run in which the ultrasonic sensors 28 are moved over one or both of the processing plates 15 containing the nucleic acids containing fluids, in which the fluid levels are determined as detailed-below in connection with FIG. 6.

The racks 3-8 are kept stationary during determining the presence of consumables and fluid levels of the fluids contained in the processing plates 15.

In the following process step (process step V), for each of the consumables to be used, the first and second signals are compared with each other in calculating a difference of the first and second signals (round-trip times or distances). The difference of the signals then is compared with an intended difference of signals as defined by the process operation plan. In case the difference of signals matches the intended difference of signal amplitudes, it is assumed that the consumable concerned is in its target position. Furthermore, determined fluid levels of fluids contained in the processing plates 15 are compared with intended fluid levels as defined by the process operation plan. In case the fluid levels match the intended fluid levels, it is assumed that the fluid levels are correct.

In case a mismatch concerning the presence of consumables is determined, a message is displayed on the display 35 containing information guiding the user to load missing and/or misplaced disposables (process step VI). In case a mismatch concerning the fluid levels is determined, another message is displayed on the display 35 containing information guiding the user to load the missing fluids (process step VI).

Otherwise, the display 35 can, e.g., display the work-plate 2 or one or more parts thereof in a manner to visualize a possible mismatch between the consumables actually present in the system 1 and the required consumables as defined by the process operation plan. Based on this visual information, the user can verify the result of the charging operation and can readily add missing consumables, e.g., by a manual charging operation.

Having loaded the missing or misplaced consumables and/or nucleic acids containing fluids, the user can re-start the subroutine "CHECK PRESENCE" and/or the subroutine "CHECK FLUID LEVELS" as desired actuating the control computer 34.

In case there is no mismatch determined, another subroutine "EXTRACTION" (process step VIII) is started for performing the steps for extracting the nucleic acids which is not further detailed herein, which ends when purified nucleic acids have be obtained (process step IX).

Figure 5B:
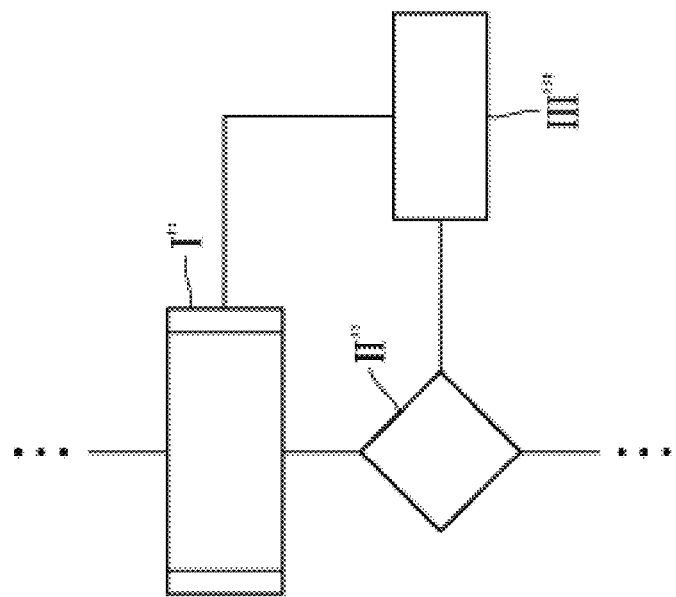
FIGS. 5A-5B are flow charts illustrating exemplary process steps which may be performed during extraction of nucleic acids according to the process operation plan.
Figure 5A:
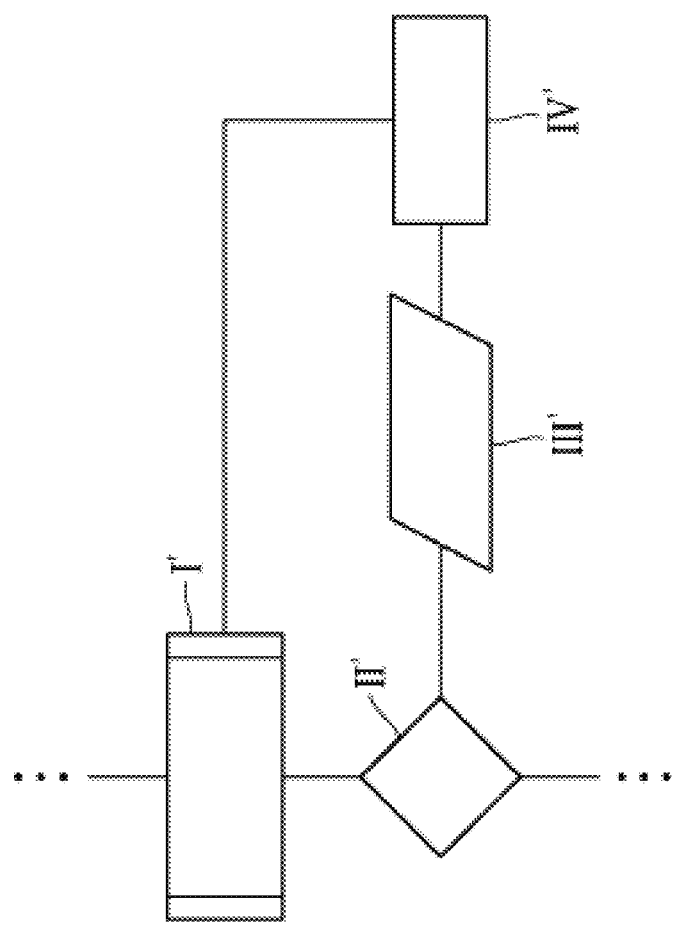

When performing the subroutine "EXTRACTION", subroutine "CHECK PRESENCE" as illustrated in FIG. 5A, and subroutine "CHECK FLUID LEVELS" as illustrated in FIG. 5B may be performed.

The symbols of the flowchart of FIG. 5A have the following meaning:
I': START SUBROUTINE "CHECK PRESENCE"
II': MISMATCH?
III': DISPLAY MESSAGE
IV': INITIATE RE-START SUBROUTINE "CHECK PRESENCE"

In case during extraction of nucleic acids arises a need of manually and/or automatically refilling of consumables, e.g., due to a low-storage capacity of the system 1, presence of refilled consumables in their intended locations has to be automatically checked prior to continuing nucleic acids extraction. Accordingly the subroutine "CHECK PRESENCE" as already above-detailed is started (process step I') to check if there is a mismatch between a difference of signal values and an intended difference of signal values (process step II') as defined by the process operation plan. In case of mismatch, a message is displayed on the display 35 (process step III'), so that the user can restart the subroutine "CHECK PRESENCE" (process step IV') actuating the control computer 34 as desired. In case of no mismatch, the subroutine "EXTRACTION" is continued.

The symbols of the flowchart of FIG. 5B have the following meaning:
I": START SUBROUTINE "CHECK FLUID LEVELS"
II": MISMATCH?
III": DISPLAY MESSAGE/INITIATE FLUID LEVEL CORRECTION/INITIATE RESTART SUBROUTINE "CHECK FLUID LEVELS"

In case of pipetting fluids during extraction of the nucleic acids, a need may arise to check the fluid level of fluids after pipetting. Accordingly the subroutine "CHECK FLUID LEVELS" as detailed below is started (process step I") to check if there is a mismatch between the actual fluid levels and the intended fluid levels (process step II") as defined by the process operation plan. In case of mismatch, a message is displayed on the display and/or the user can initiate an automated fluid level correction and/or the user can restart the subroutine "CHECK FLUID LEVELS" actuating the control computer 34. In case of no mismatch, the subroutine "EXTRACTION" is continued.

Accordingly, prior to starting and/or during nucleic acids containing fluid processing, the presence of consumables to be used for the processing of fluids in intended positions as defined by the process operation plan is controlled scanning the consumables by means of the ultrasonic sensors 28.

Additionally, an identity and/or orientation of individual consumables with respect to their intended positions as defined by the process operation plan may be performed, e.g., determining a geometric profile, in particular a height profile (height pattern), of individual objects which is compared with an intended profile for the consumable concerned.

Due to the linear sensor array 27, adapted to the rows of the planar arrays of plates and trays, presence of consumables contained therein and/or fluid levels of fluids contained therein may be efficiently controlled in parallel when moving the sensor array 27 along the stacking direction of rows and simultaneously determining the presence of objects and/or fluid levels.

Intended signal values as defined by the process operation plan may be readily adapted in calibrating the ultrasonic sensor signals using reference surfaces of the racks and plates, respectively.

Figure 6:
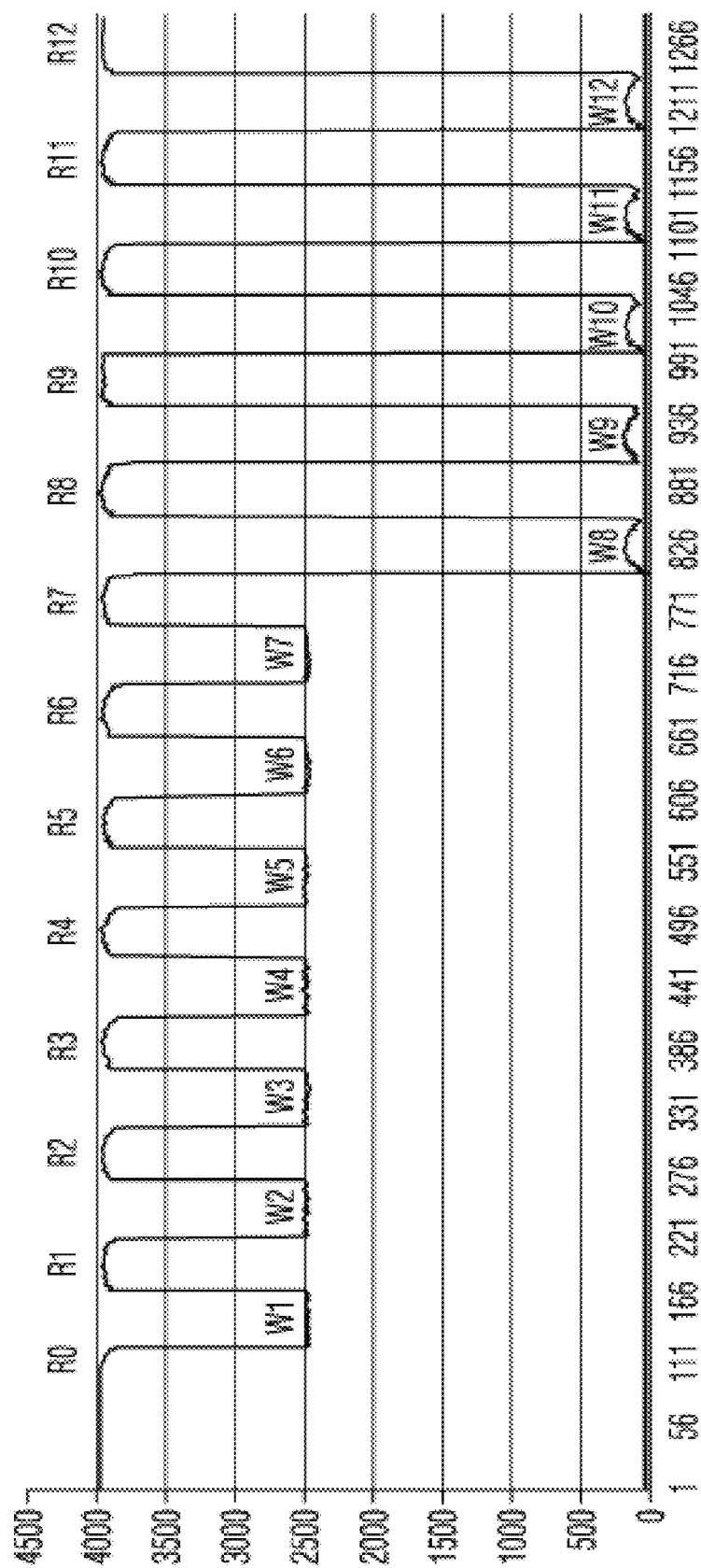
FIG. 6 is a diagram depicting a time-of-travel curve for determining liquid levels in the system of FIG. 1.

Reference is now made to FIG. 6 illustrating a diagram depicting a time-of-travel indicating curve for determining fluid levels in the output plate 16 using the sensor array 27 of the system 1.

Specifically, FIG. 6 indicates time-of-travel measurements of an ultrasonic sensor 28 which is continuously moved along the second direction (stacking direction of rows) as indicated by arrow 32 (see FIG. 1) of the output plate 16. The x-axis of this diagram is indicating a travel time of the positioning device which relates to a position on the process area given a reference/starting position of the positioning device and its velocity. The time-of-travel measurements are obtained in transmitting acoustic waves towards the output plate 16 and receiving the acoustic waves upon reflection to thereby determine a time interval between transmitted and received acoustic waves. The y-axis of this diagram depicts the turn-around time of an acoustic wave emitted by the ultrasonic sensor, reflected (vertically) from the location of the process area underneath and received by the ultrasonic sensor. Accordingly, a time-of-travel profile of the output plate 16 as seen by the ultrasonic sensor 28 is obtained.

When interpreting the time-of-travel profile of FIG. 6, positions of individual wells along the second direction can be determined based on a detection of falling and rising edges with respect to a reference level (R0 to R12) which corresponds to the plane level of the output plate 16. Having identified each of the wells, well levels W1 to W12 in-between adjacent falling and rising edges corresponding to fluid levels in the wells are determined, for instance, e.g., using the mean function or the highest value between the edges. Accordingly, as a result of above analysis, the output plate 16 is determined to include seven half-full wells and five empty wells.

Using the ultrasonic sensors 28 of the linear sensor array 27 in a way as exemplified in FIG. 6 for a single ultrasonic sensor 28, all wells of the output plate 16 can be efficiently scanned with respect to fluid level detection in a single run.

Alternatively, the sensor array 27 may be continuously moved along the first direction (direction according to which wells are arranged in individual rows) as indicated by arrow 33 (see FIG. 1) of the output plate 16. Yet alternatively, the sensor array 27 may continuously moved to perform a combined movement along the first and second directions of the output plate 16.

Combining movements of the pipetting tips 22 for pipetting of liquids for the automated extraction of nucleic acids with movements of the ultrasonic sensors 28 for detecting of fluid levels, the outcome of pipetting operations may be efficiently controlled by fluid level detection, for instance, in performing pipetting operations when moving the transfer head 29 in one direction of travel and performing fluid levels detection when moving the transfer head 29 in an opposite direction of travel. More particularly, when determining fluid levels prior to pipetting operations and also after the pipetting operations, pipetted volumes may be determined. Basically, information obtained in scanning along one dimension can be considered sufficient in case consumables are symmetrically arranged along such scanning directions.

Figure 7:
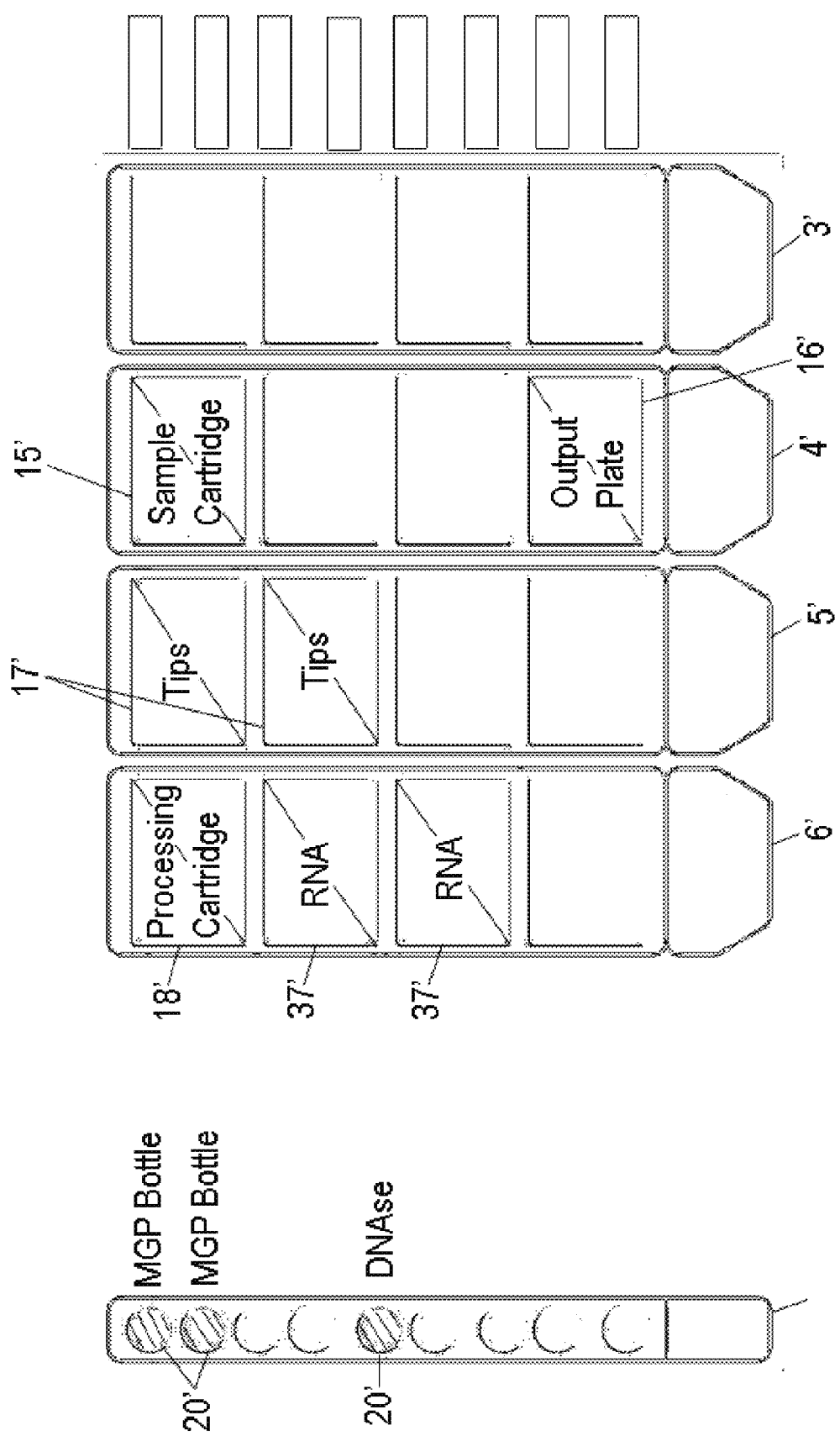
FIG. 7 is an exemplary screen display of target positions of objects.

FIG. 7 depicts an exemplary screen display of the display 35 of target positions of objects. A process operation plan according to this embodiment comprises a section for supporting the loading of objects onto the work-plate 2 of the system 1. As described in respect of FIGS. 4 and 5 the user of the control computer 34 selects a process operation plan from a menu. The process operation plan then continues and displays the objects to be loaded on a screen display as shown in FIG. 7. It can be seen that the screen display is a schematic representation of the work-plate 2 as shown in FIG. 2. Reference numerals in FIG. 7 have a dash to indicate that the numbers are used for screen representations of like objects in FIG. 2.

As can be seen in FIG. 7 the user is instructed by the screen display to load bottles 20' which are MGP bottles (i.e. bottles holding a suspension of magnetic glass particles) and DNAse reagent bottles (i.e. a DNA digesting reagent) into the indicated positions (target positions) in the bottle rack 8'. Further the first reagent rack 6' needs to be filled with the reagent plate 18' (processing cartridge) and two specific reagents 37'. The tip tray rack 5' needs to be filled with two tip trays 17' prefilled with tips and the processing rack 4' is to be filled with the processing plate 15' (sample cartridge) and the output plate 16'. When the user has disposed the objects accordingly he can press an OK button and the control computer 34 proceeds with the process operation plan. As described above it is checked with one or more ultrasonic sensors 28 if objects are present in the prescribed positions. As also described before, it may be further checked by the profile of the objects if proper objects have been loaded. By this it can be for example detected when tips have been loaded in a position for reagents.

Loading mistakes can be signalled to the user by e.g. text messages as "please load tips" or "sample cartridge is missing".

Further a similar screen display as depicted in FIG. 7 can be employed to signal loading mistakes by colour coded representation of missing objects or misplaced objects. E.g. a missing tip tray can be depicted in red and flashing.

Accordingly, by the above discussion, a system 1 for the automated processing of fluids according to a process operation plan involving the use of preloaded objects, in which the process operation plan defines preloaded objects to be present in target object positions, has been disclosed. The system comprises: a processing area 2 in which objects 13-20 to be used for the processing of fluids are located; at least one ultrasonic sensor 28, adapted for determining the presence of objects 13-20 by means of acoustical waves; a positioning device 23 to which the ultrasonic sensor 28 is fixed, adapted to move the ultrasonic sensor 28 in at least one direction relative to said processing area 2; a control computer 34 being configured to determine the presence of objects 13-20 and determining if objects 13-20 are present in target object positions (e.g., retaining sections 12) in said processing area 2 as defined by said process operation plan; at least one pipetting device 21, 26 for pipetting of fluids between cavities located in said processing area 2; and an analytical or pre-analytical processing device 36 for processing of fluids located in said processing area 2.

In another embodiment, the system 1 further comprises a plurality of ultrasonic sensors 28 arranged in a sensor array 27, said control computer 34 being configured to simultaneously determine the presence of objects 13-20 and determining if objects are present in said target object positions 12 as defined by said process operation plan.

In another embodiment, the system 1 further comprises a signalizing device 35, wherein said control computer 34 being configured to signalize a mismatch between objects present and objects required in said target object positions 12 as defined by said process operation plan.

In another embodiment, the signalizing device is a display 35, and the control computer 34 is configured to display a representation of one or more parts of said system 1 in order to visualize said target object positions 12 as defined by said process operation plan.

In another embodiment, the system 1 further comprises at least one holder 3-8, adapted to hold said preloaded objects 13-20 in said target object positions 12.

In another embodiment, a method has been disclosed for determining the matching of objects present in a processing area 2 in an instrument 1 (system) with preloaded objects to be present in target object positions 12 in said instrument according to a process operation plan. The method comprises the following steps: determining the presence of objects 13-20 relative to the processing area 2 in said instrument by means of at least one ultrasonic sensor 28; and determining if objects 13-20 are present in target object positions 12 as defined by said process operation plan.

In another embodiment, the method further includes a step of outputting a message to a signalizing device 35 based on a result of said determination if objects are present in said target object positions 12 as defined by said process operation plan.

In another embodiment, the method further includes a step of displaying a representation of one or more parts of the system 1 in order to visualize the target object positions 12 as defined by said process operation plan.

In another embodiment, the method further includes a step of displaying a mismatch between objects present and objects required in said target object positions 12 as defined by said process operation plan.

In another embodiment, the message contains user-guiding information about objects 13-20 to be loaded in target object positions 12 into said instrument 1.

In another embodiment, the method further including a step of determining identity and/or orientation relative to said instrument 1 of objects 13-20 present in said instrument.

In another embodiment, determining the presence of objects 13-20 relative to said instrument by said at least one ultrasonic sensor 28 involves moving of the ultrasonic sensor, wherein moving of the ultrasonic sensor is combined with moving of a pipetting device 21 for pipetting of fluids.

In another embodiment, the method further includes a step of determining of fluid levels of fluids contained in cavities by means of said at least one ultrasonic sensor 28.

In another embodiment, determining of fluid levels involves measuring of distance values of said cavities with respect to a reference distance level as defined by a plane said cavities are arrayed in.

In still another embodiment, a method for the automated processing of fluids according to a process operation plan involving the use of preloaded objects, comprises utilizing any of the above described methods according to the present invention.

Obviously many modifications and variations of the present invention are possible in light of the above description. It is therefore to be understood, that within the scope of appended claims, the invention may be practiced otherwise than as specifically devised.

What is claimed is:

1. A method for automatically processing a plurality of runs of liquid samples, comprising:
   providing an instrument including a control computer, a display, at least one ultrasonic sensor, and a processing area, wherein the instrument carries out a process operation plan requiring a plurality of preloaded consumables to be present in a corresponding plurality of target positions of a rack into which consumables are to be placed when preloaded prior to processing the liquid samples, the rack being located in the processing area;
   detecting, using the control computer, liquid levels of the liquid samples based on a plurality of first signals from the at least one ultrasonic sensor;
   determining, using the control computer, whether the plurality of preloaded consumables are present in the corresponding plurality of target positions of the rack based on a plurality of second signals from the at least one ultrasonic sensor, wherein the plurality of runs includes at least one run wherein all of the plurality of preloaded consumables are present in the corresponding plurality of target positions and at least one run wherein one or more of the plurality of preloaded consumables are not present in the corresponding plurality of target positions;
   in response to determining that all of the plurality of preloaded consumables are present in the corresponding plurality of target positions, the instrument automatically processing the liquid samples using the plurality of preloaded consumables according to the process operation plan, wherein automatically processing the liquid samples includes bringing the plurality of preloaded consumables into contact with the liquid samples; and
   in response to determining that one or more of the plurality of preloaded consumables is not present in the corresponding plurality of target positions, the control computer causing the display to display a mismatch between preloaded consumables actually present in the corresponding plurality of target positions and preloaded consumables not present in the corresponding plurality of target positions.

2. The method according to claim 1, further comprising displaying on the display a representation of the processing area to permit a user to visualize the target positions as defined by the process operation plan.

3. The method according to claim 1, wherein the displayed mismatch contains user-guiding information about the preloaded consumables not present in the corresponding plurality of target positions.

4. The method according to claim 1, wherein determining includes moving the at least one ultrasonic sensor over the corresponding plurality of target positions, and wherein moving the at least one ultrasonic sensor is combined with moving a pipetting device of the instrument for pipetting of the liquid samples.

5. The method according to claim 1, wherein detecting liquid levels of the liquid samples includes measuring distances to the liquid levels and comparing the distances to a reference distance.

6. The method according to claim 5, further comprising determining the reference distance using the control computer by measuring a time between emission for an acoustic wave from the at least one ultrasonic sensor and reception of an acoustic wave reflected off a reference surface of the instrument.

7. The method according to claim 1, wherein the at least one ultrasonic sensor includes a linear sensor array including a plurality of ultrasonic sensors coupled to the instrument in spaced apart relationship corresponding to the corresponding plurality of target positions and moveable in together to simultaneously generate the plurality of second signals from which the presence of the plurality of preloaded consumables in the corresponding plurality of target positions is determined.

* * * * *